(12) United States Patent
Hanawa

(10) Patent No.: US 11,382,491 B2
(45) Date of Patent: Jul. 12, 2022

(54) ENDOSCOPE, DISTAL END STRUCTURE OF ENDOSCOPE AND METHOD FOR MODIFYING DISTAL END STRUCTURE OF ENDOSCOPE

(71) Applicant: OLYMPUS CORPORATION, Tokyo (JP)

(72) Inventor: Tetsuta Hanawa, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 97 days.

(21) Appl. No.: 16/893,545

(22) Filed: Jun. 5, 2020

(65) Prior Publication Data

US 2020/0297192 A1  Sep. 24, 2020

Related U.S. Application Data

(63) Continuation of application No. PCT/JP2018/038508, filed on Oct. 16, 2018.

(30) Foreign Application Priority Data

Dec. 6, 2017  (JP) .............................. JP2017-234230

(51) Int. Cl.
  *A61B 1/00*  (2006.01)
  *A61B 1/018*  (2006.01)
  (Continued)

(52) U.S. Cl.
  CPC ...... *A61B 1/00098* (2013.01); *A61B 1/00133* (2013.01); *A61B 1/018* (2013.01); *A61B 1/05* (2013.01); *A61B 1/0669* (2013.01)

(58) Field of Classification Search
  CPC .............. A61B 1/0008; A61B 1/00087; A61B 1/00089; A61B 1/00096; A61B 1/00098;
  (Continued)

(56) References Cited

U.S. PATENT DOCUMENTS 5,019,121 A * 5/1991 Krauter .................. A61B 1/008
                                                     600/137
2003/0040657 A1  2/2003 Yamaya et al.
(Continued)

FOREIGN PATENT DOCUMENTS

JP  2003-339633 A  12/2003
JP  2005-254002 A   9/2005
(Continued)

OTHER PUBLICATIONS

International Search Report dated Dec. 4, 2018 issued in PCT/JP2018/038508.

*Primary Examiner* — Ryan N Henderson
*Assistant Examiner* — Pamela F Wu
(74) *Attorney, Agent, or Firm* — Scully, Scott, Murphy & Presser, P.C.

(57) ABSTRACT

An endoscope includes a fixed barrel non-turnably provided at a distal end portion of an insertion portion, an image pickup unit held to the fixed barrel, a movable barrel including a channel holding hole for holding a distal end of a treatment instrument channel inserted through the insertion portion, the movable barrel being supported by the fixed barrel so as to be turnable around an optical axis of the image pickup unit and being located closer to a distal end side than the fixed barrel, and a power transmission mechanism that transmits, to the movable barrel, power for causing the movable barrel to turn.

12 Claims, 18 Drawing Sheets

(51) Int. Cl.
*A61B 1/05* (2006.01)
*A61B 1/06* (2006.01)

(58) Field of Classification Search
CPC ............ A61B 1/00101; A61B 1/00133; A61B 1/00137; A61B 1/018; A61B 1/05; A61B 1/012; A61B 1/053; A61B 1/0016; A61B 1/00135
USPC .................. 600/104, 106–107, 127, 129, 175
See application file for complete search history.

(56) References Cited

U.S. PATENT DOCUMENTS

| | | | | |
|---|---|---|---|---|
| 2006/0167342 | A1* | 7/2006 | Bob ..................... | A61B 1/0053 |
| | | | | 600/137 |
| 2007/0255096 | A1* | 11/2007 | Stefanchik ........... | A61B 1/0008 |
| | | | | 600/106 |
| 2010/0056861 | A1* | 3/2010 | Spivey ................... | A61B 1/018 |
| | | | | 600/106 |

FOREIGN PATENT DOCUMENTS

| | | |
|---|---|---|
| JP | 2014-161645 A | 9/2014 |
| JP | 2016-150103 A | 8/2016 |

\* cited by examiner

ENDOSCOPE, DISTAL END STRUCTURE OF ENDOSCOPE AND METHOD FOR MODIFYING DISTAL END STRUCTURE OF ENDOSCOPE

CROSS REFERENCE TO RELATED APPLICATION

This application is a continuation application of PCT/JP2018/038508 filed on Oct. 16, 2018 and claims benefit of Japanese Application No. 2017-234230 filed in Japan on Dec. 6, 2017, the entire contents of which are incorporated herein by this reference.

BACKGROUND OF THE INVENTION

1. Field of the Invention

The present invention relates to an endoscope including a treatment instrument channel for allowing insertion of a treatment instrument, a distal end structure of the endoscope and a method for modifying the distal end structure of the endoscope.

2. Description of the Related Art

Conventionally, endoscopes have been widely used in medical and industrial fields and the like, which observe a subject/object by inserting an elongated insertion portion into the subject/object and can perform various types of treatment using a treatment instrument as required.

When treatment using such an endoscope is performed, a position of the treatment instrument caused to protrude from a distal end opening portion of a treatment instrument channel with respect to a target site such as an affected area under endoscopic observation is adjusted by bending a bending portion and moving the insertion portion in an insertion/removal direction or the like.

In order to improve operability and workability in such position adjustment, for example, Japanese Patent Application Laid-Open Publication No. 2005-254002 discloses a configuration including an observation optical system, an insertion portion in which a treatment instrument channel is formed, a bending portion disposed on a distal end side of the insertion portion, and a bending operation portion disposed on a proximal end side of the insertion portion and enabled to operate the bending portion, in which the insertion portion is provided so as to be turnable with respect to the bending operation portion.

SUMMARY OF THE INVENTION

An endoscope according to an aspect of the present invention includes a fixed barrel non-turnably provided at a distal end portion of an insertion portion, an image pickup unit held to the fixed barrel, a movable barrel including a holding hole for holding a distal end of a treatment instrument channel inserted through the insertion portion, the movable barrel being supported by the fixed barrel so as to be turnable around an optical axis of the image pickup unit and being located closer to a distal end side than the fixed barrel, and a power transmission mechanism that transmits, to the movable barrel, power for causing the movable barrel to turn.

A distal end structure of an endoscope according to another aspect of the present invention includes a fixed barrel provided at a distal end of an insertion portion of the endoscope, an image pickup unit held to the fixed barrel, a movable barrel provided closer to a distal end side than the fixed barrel, the movable barrel including a holding hole for holding a distal end of a treatment instrument channel inserted through the insertion portion and being supported by the fixed barrel so as to be turnable in a circumferential direction of the image pickup unit with respect to the image pickup unit, and a power transmission mechanism that transmits, to the movable barrel, power for causing the movable barrel to turn.

A method for modifying a distal end structure of an endoscope according to another aspect of the present invention is applied to a distal end structure of an endoscope including a fixed barrel provided at a distal end of an insertion portion of the endoscope, an image pickup unit held to the fixed barrel, a movable barrel provided closer to a distal end side than the fixed barrel, the movable barrel including a holding hole for holding a distal end of a treatment instrument channel inserted through the insertion portion and being supported by the fixed barrel so as to be turnable in a circumferential direction of the image pickup unit with respect to the image pickup unit, and a power transmission mechanism that transmits, to the movable barrel, power for causing the movable barrel to turn, the method including causing the movable barrel to turn via the power transmission mechanism without causing the image pickup unit held to the fixed barrel to turn and moving a treatment instrument protruding from the treatment instrument channel by turning the movable barrel and causing the treatment instrument to access a target site.

DETAILED DESCRIPTION OF THE PREFERRED EMBODIMENTS

Figure 2:
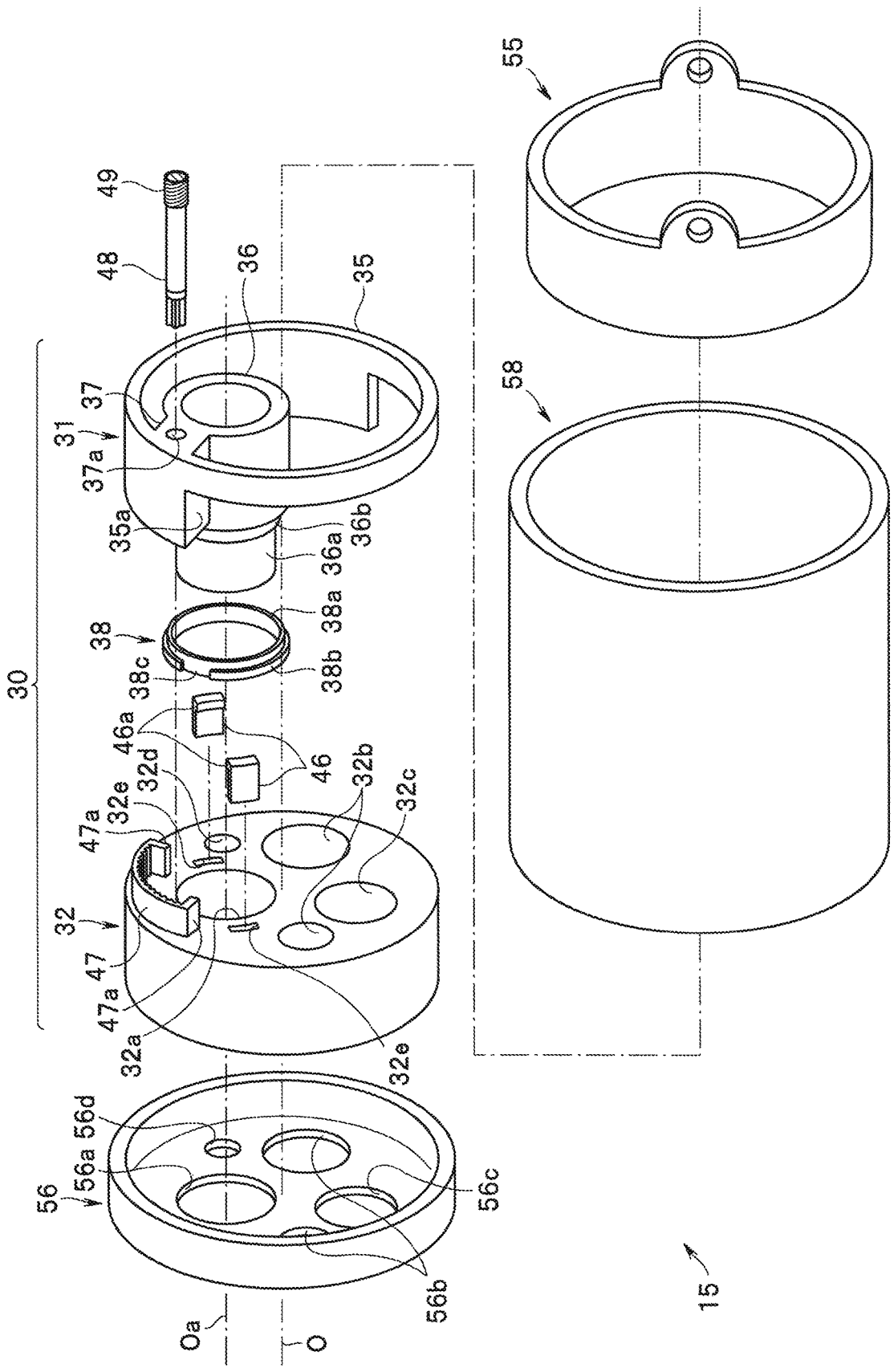
FIG. 2 is an exploded perspective view of a distal end portion.
Figure 3:
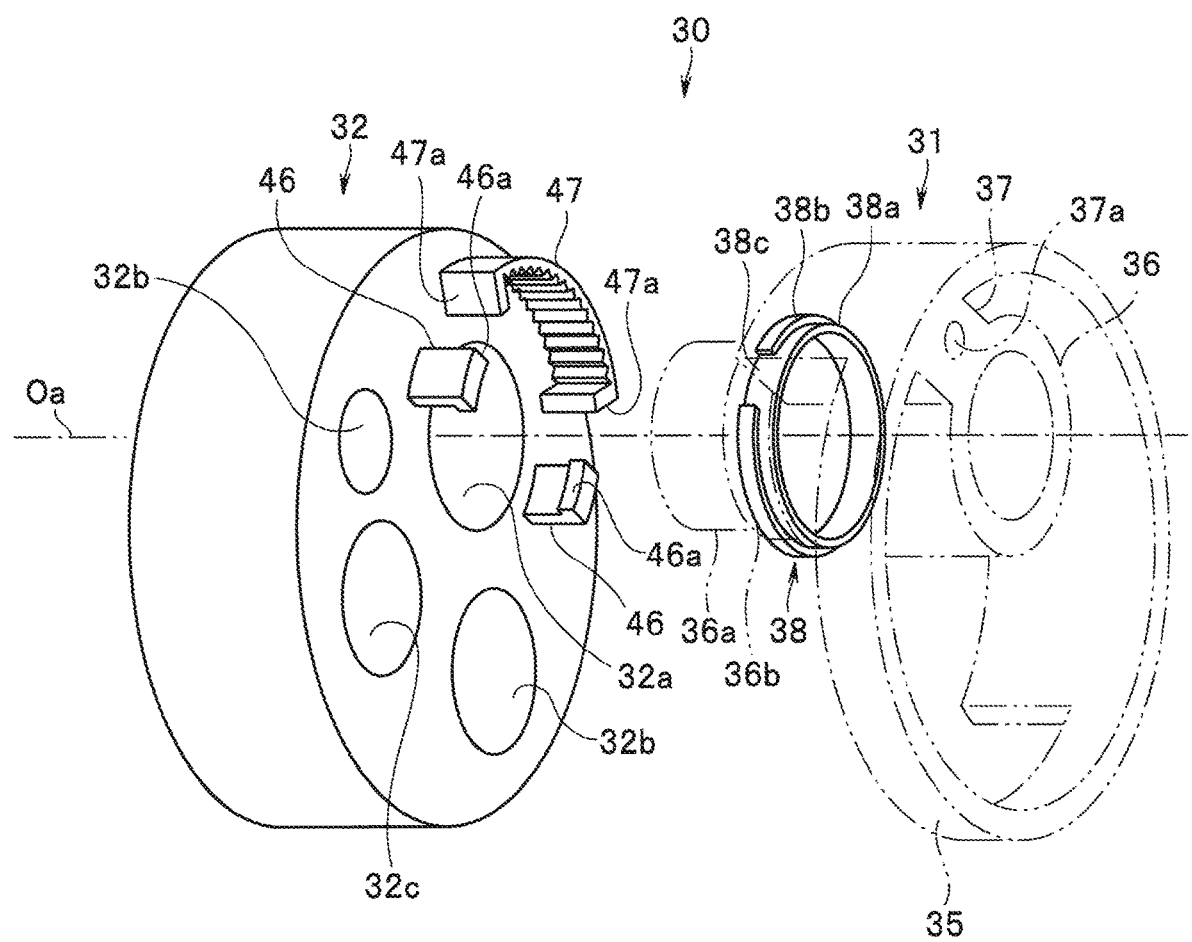
FIG. 3 is a perspective view illustrating a stopper ring and a movable barrel held to a fixed barrel.
Figure 4:
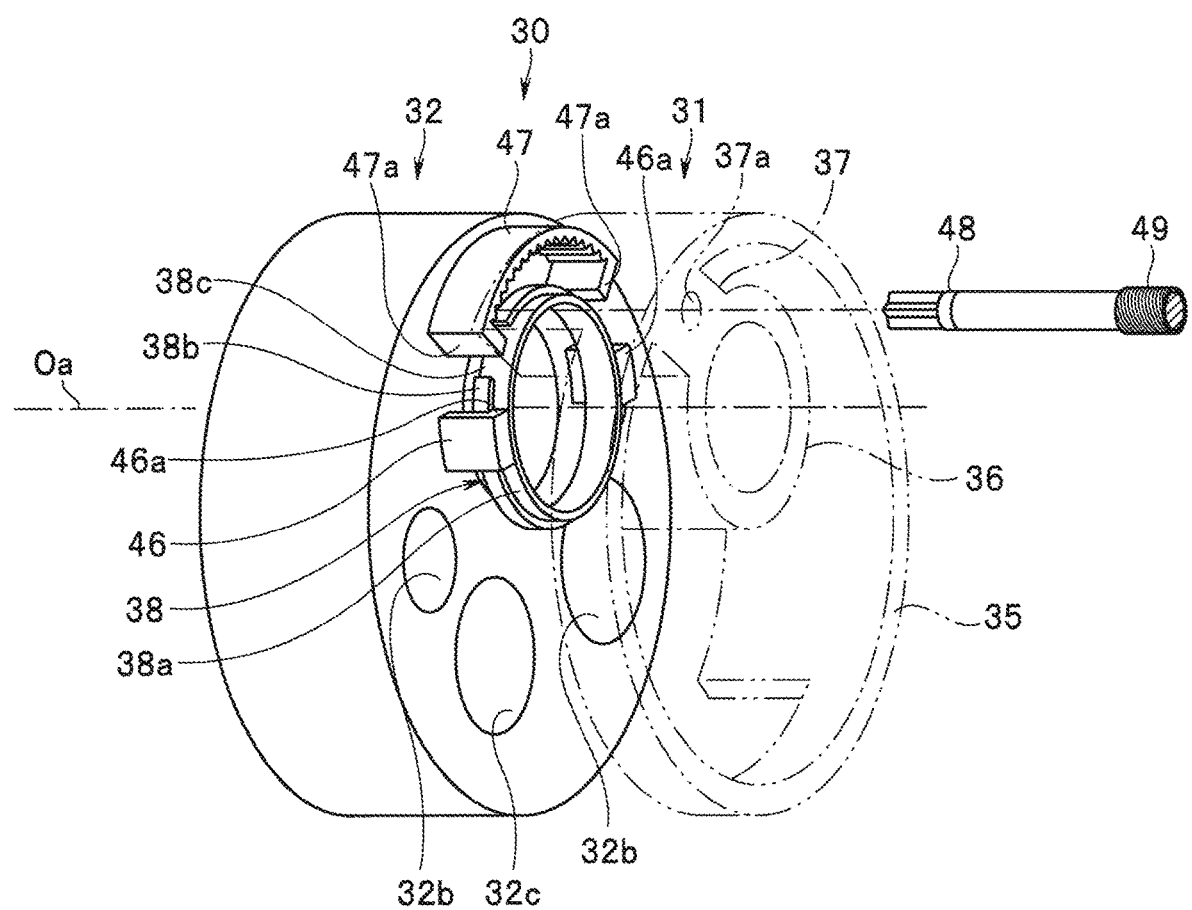
FIG. 4 is a perspective view illustrating a pinion supported by the fixed barrel and a movable barrel.
Figure 5:
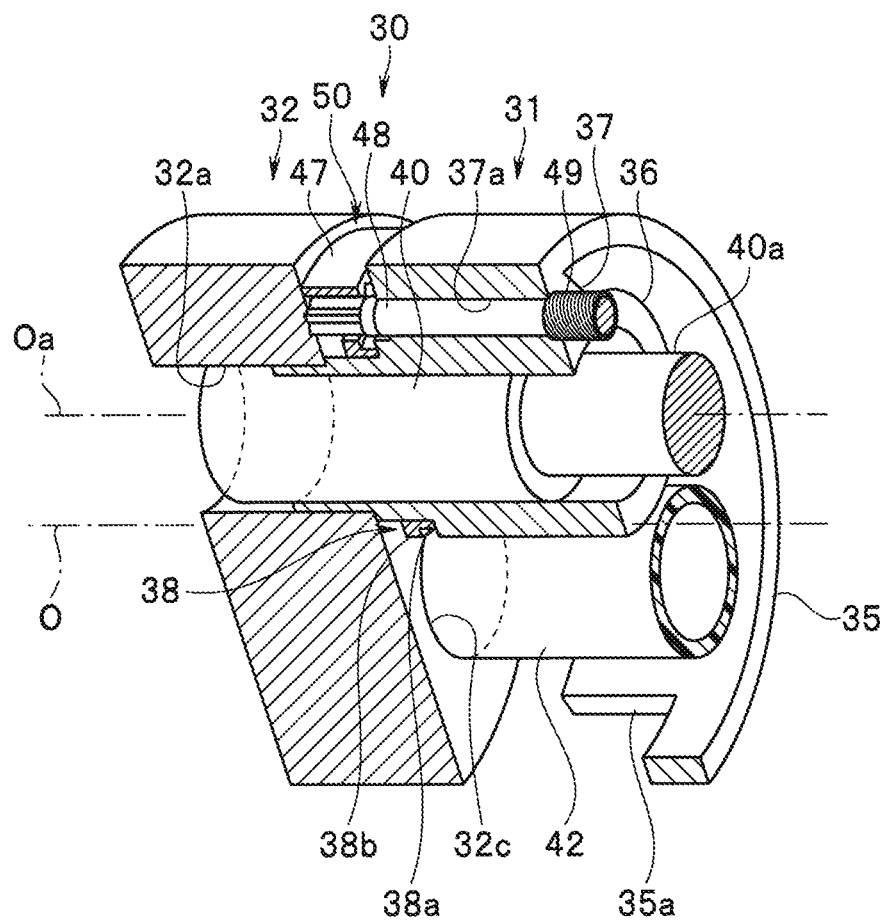
FIG. 5 is a cross-sectional view of main parts of a variable distal end portion body.
Figure 6:
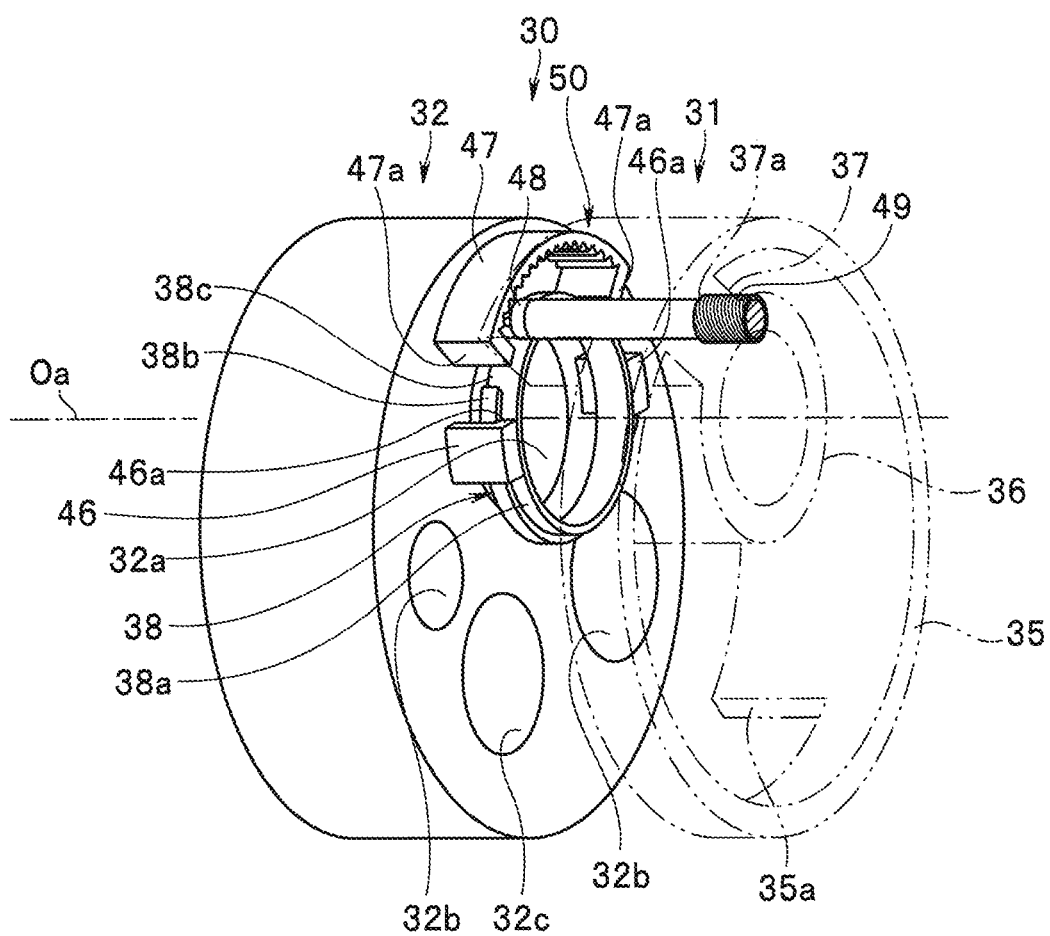
FIG. 6 is a perspective view illustrating a relationship between a rack and the pinion when the movable barrel is located at a reference position.
Figure 7:
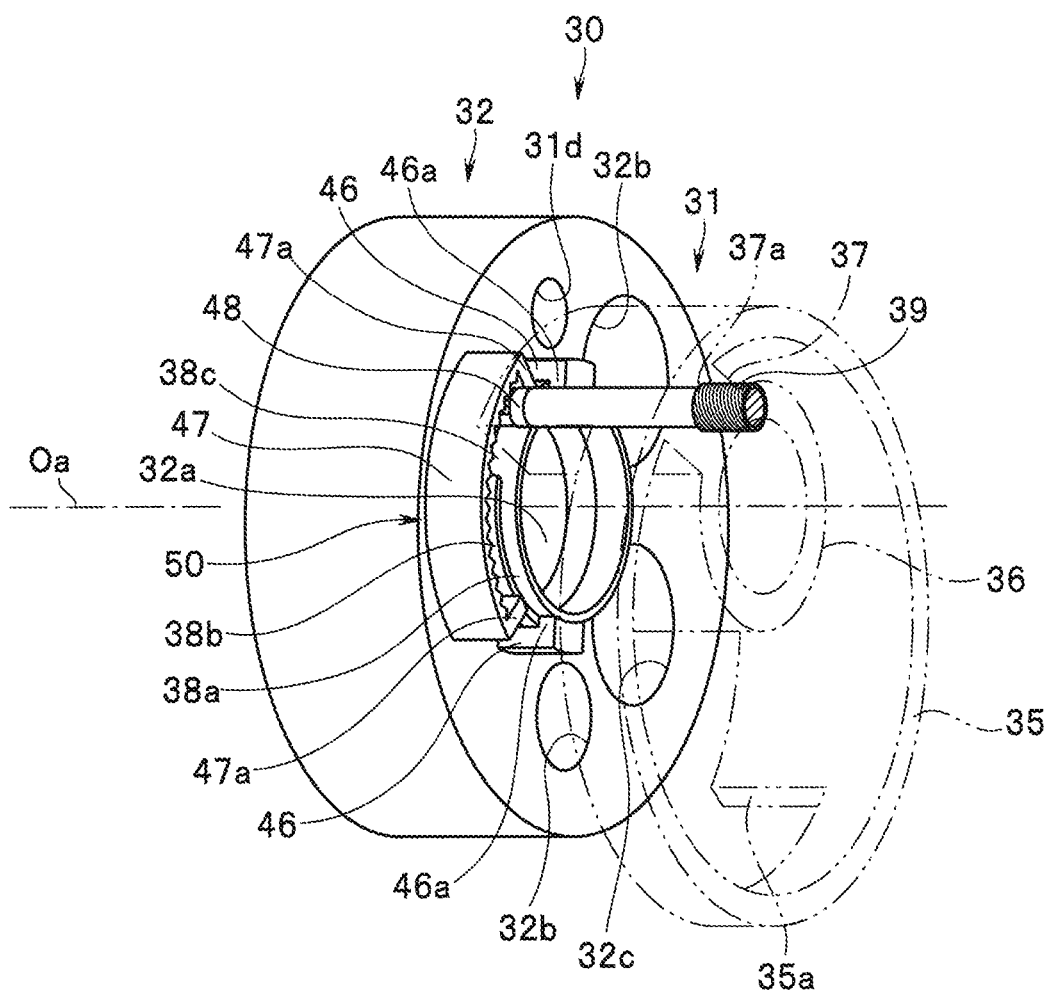
FIG. 7 is a perspective view illustrating a relationship between the rack and the pinion when the movable barrel is located at a maximum turning position.
Figure 8:
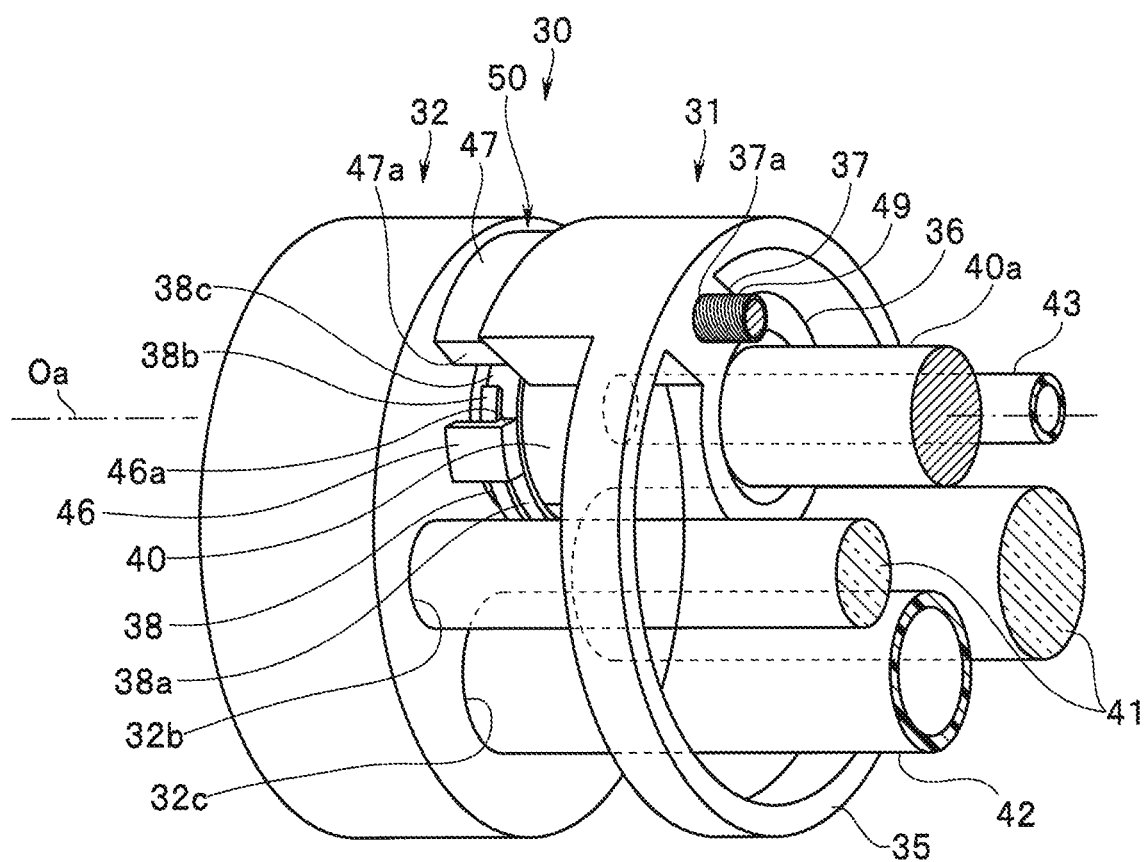
FIG. 8 is an explanatory diagram illustrating a state of each internal component when the movable barrel is located at the reference position.
Figure 9:
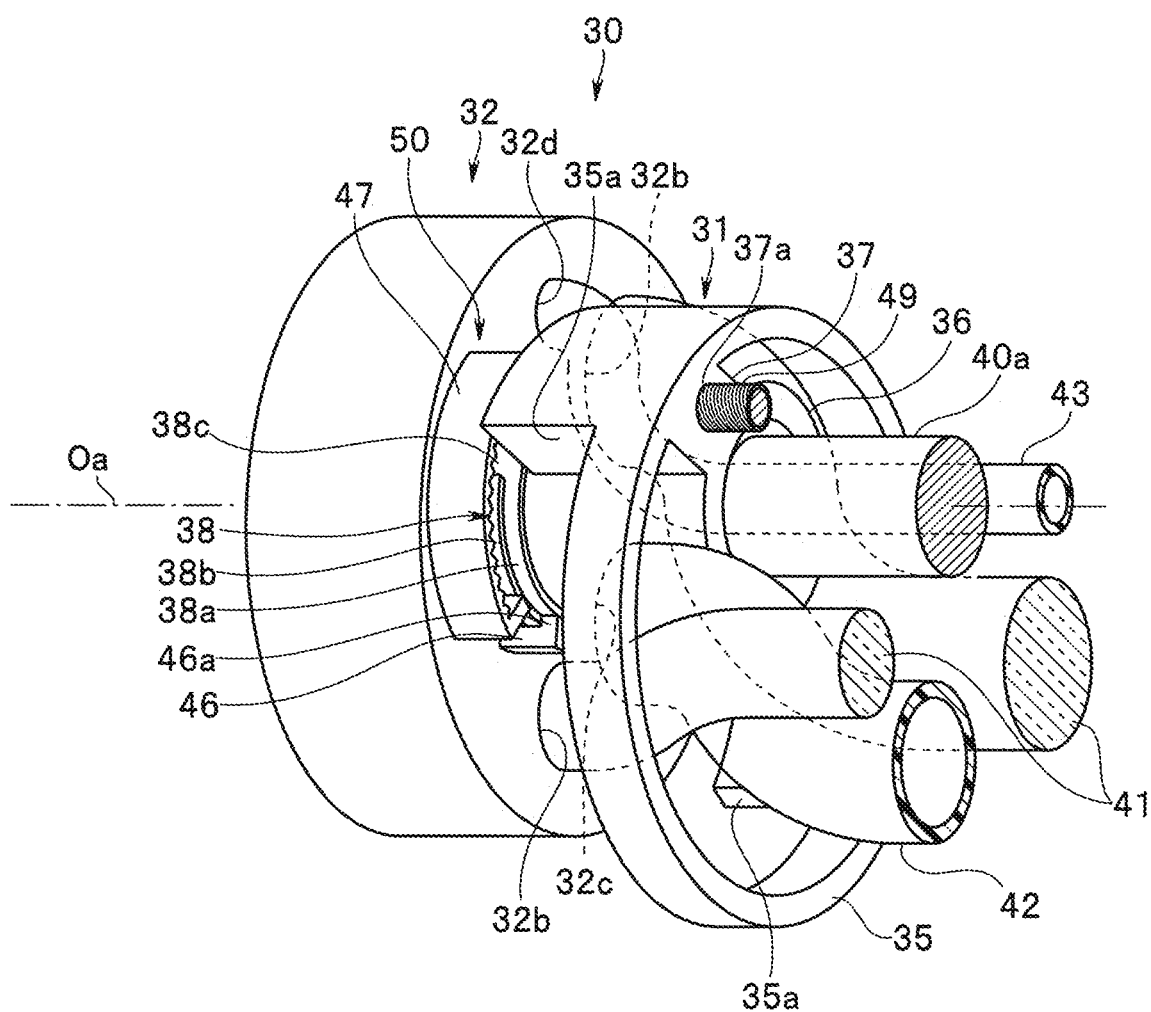
FIG. 9 is an explanatory diagram illustrating a state of each internal component when the movable barrel is located at the maximum turning position.
Figure 10:
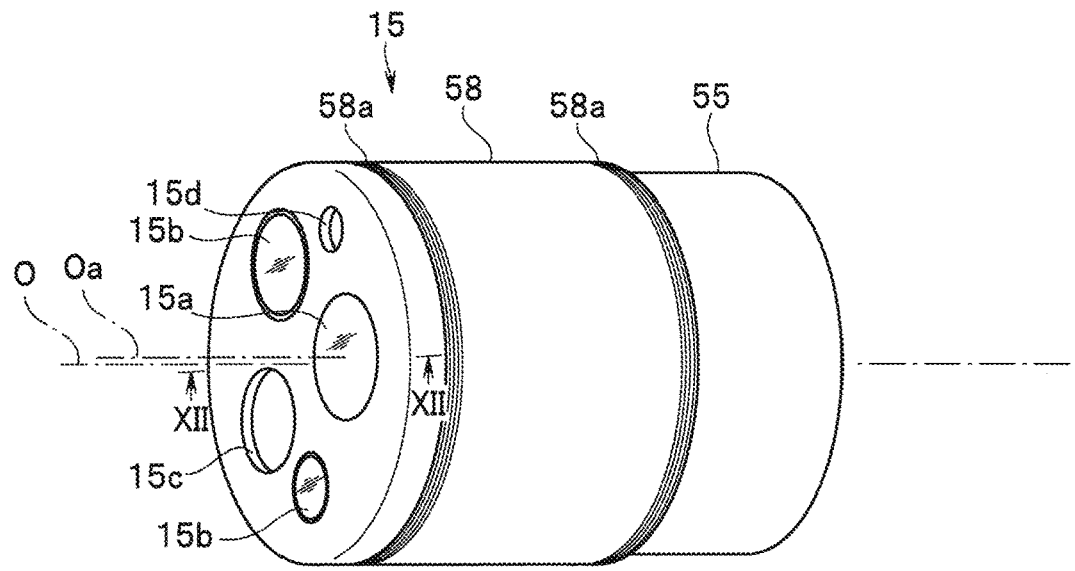
FIG. 10 is a perspective view illustrating an appearance of the distal end portion when the movable barrel is located at the reference position.
Figure 11:
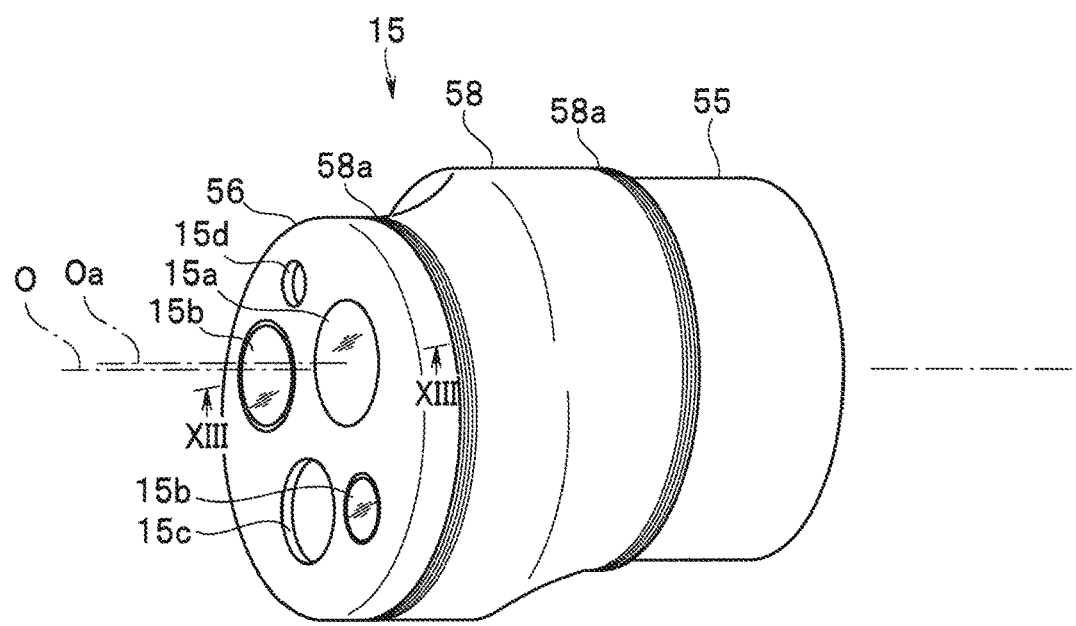
FIG. 11 is a perspective view illustrating an appearance of the distal end portion when the movable barrel is located at the maximum turning position.
Figure 12:
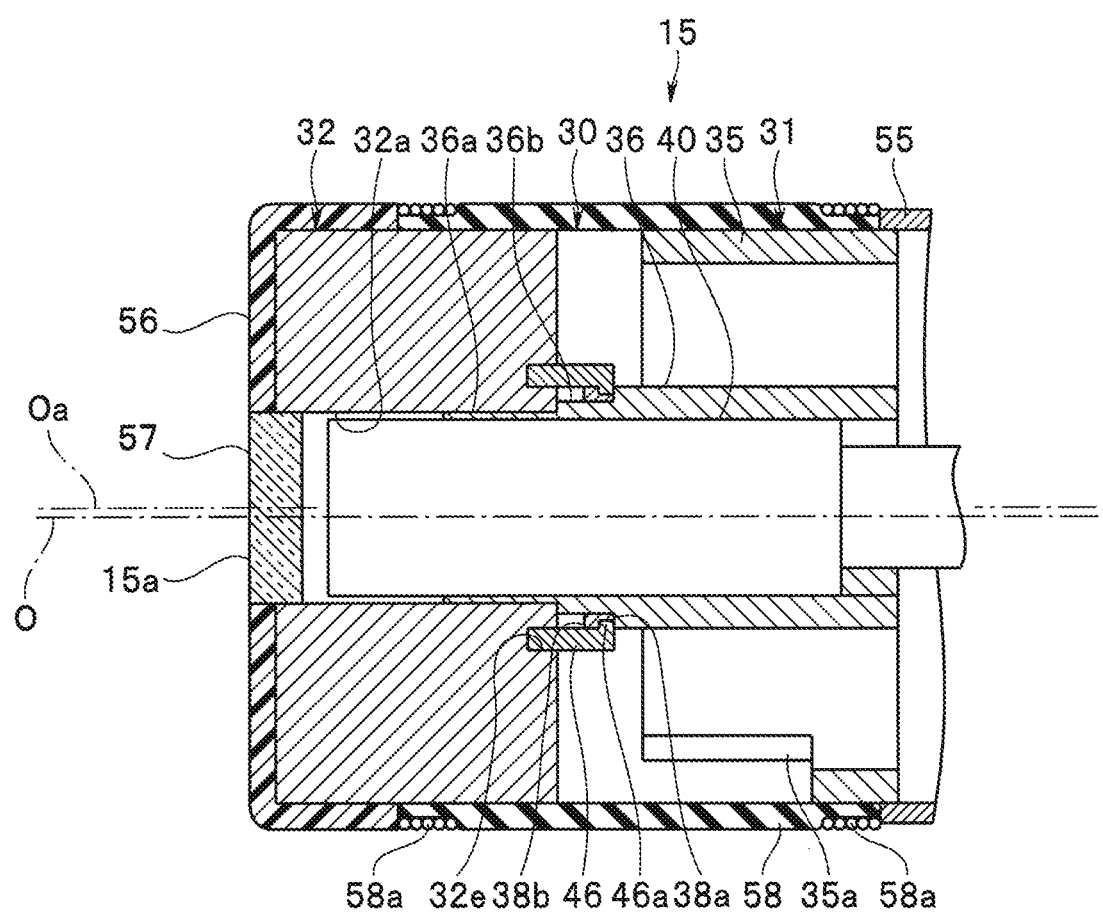
FIG. 12 is a cross-sectional view along XII-XII in FIG. 10.
Figure 13:
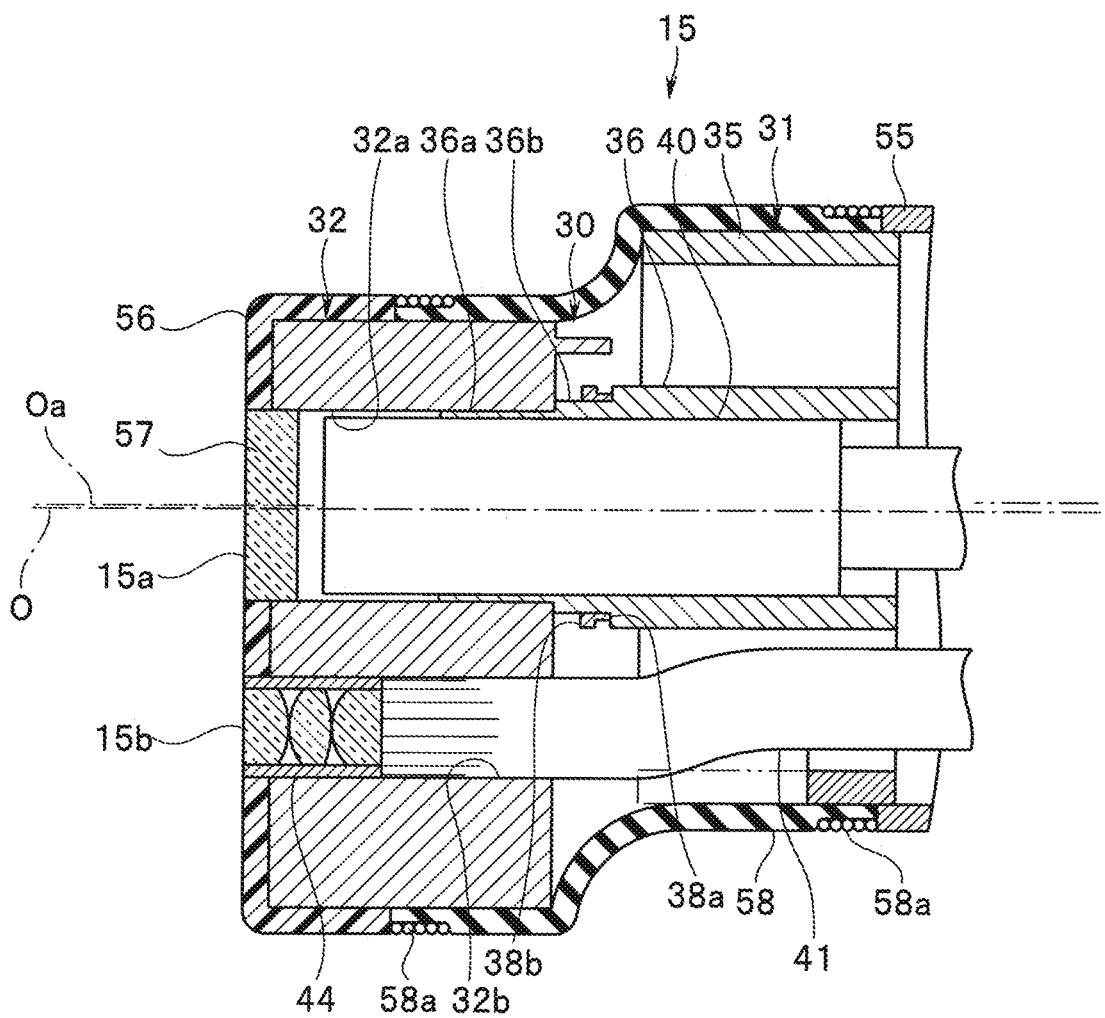
FIG. 13 is a cross-sectional view along XIII-XIII in FIG. 11.
Figure 14:
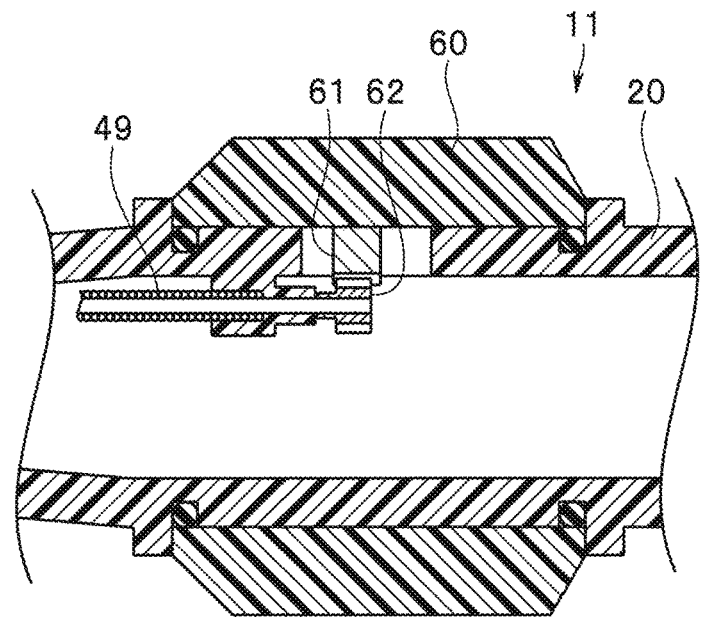
FIG. 14 is a cross-sectional view illustrating a distal end barrel drive mechanism provided in an operation portion.
Figure 15:
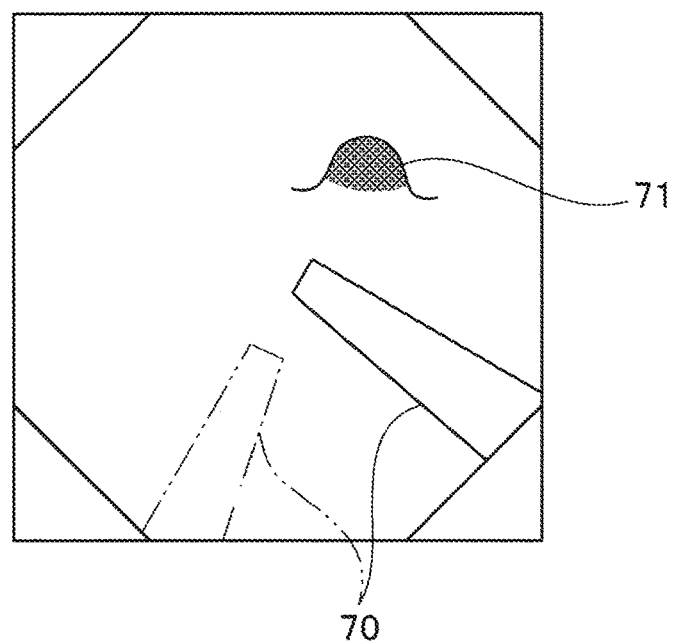
FIG. 15 is a schematic view of an endoscopic image.

Hereinafter, embodiments of the present invention will be described with reference to the accompanying drawings. The drawings relate to an embodiment of the present invention, in which FIG. 1 is a schematic configuration diagram of an endoscope system, FIG. 2 is an exploded perspective view of a distal end portion, FIG. 3 is a perspective view illustrating a stopper ring and a movable barrel held to a fixed barrel, FIG. 4 is a perspective view illustrating a pinion supported by the fixed barrel and the movable barrel, FIG. 5 is a cross-sectional view of main parts of a variable distal end portion body, FIG. 6 is a perspective view illustrating a relationship between a rack and the pinion when the movable barrel is located at a reference position, FIG. 7 is a perspective view illustrating a relationship between the rack and the pinion when the movable barrel is located at a maximum turning position, FIG. 8 is an explanatory diagram illustrating a state of each internal component when the movable barrel is located at the reference position, FIG. 9 is an explanatory diagram illustrating a state of each internal component when the movable barrel is located at the maximum turning position, FIG. 10 is a perspective view illustrating an appearance of the distal end portion when the movable barrel is located at the reference position, FIG. 11 is a perspective view illustrating an appearance of the distal end portion when the movable barrel is located at the maximum turning position, FIG. 12 is a cross-sectional view along XII-XII in FIG. 10, FIG. 13 is a cross-sectional view along XIII-XIII in FIG. 11, FIG. 14 is a cross-sectional view illustrating a distal end barrel drive mechanism provided in an operation portion, and FIG. 15 is a schematic view of an endoscopic image.

Figure 1:
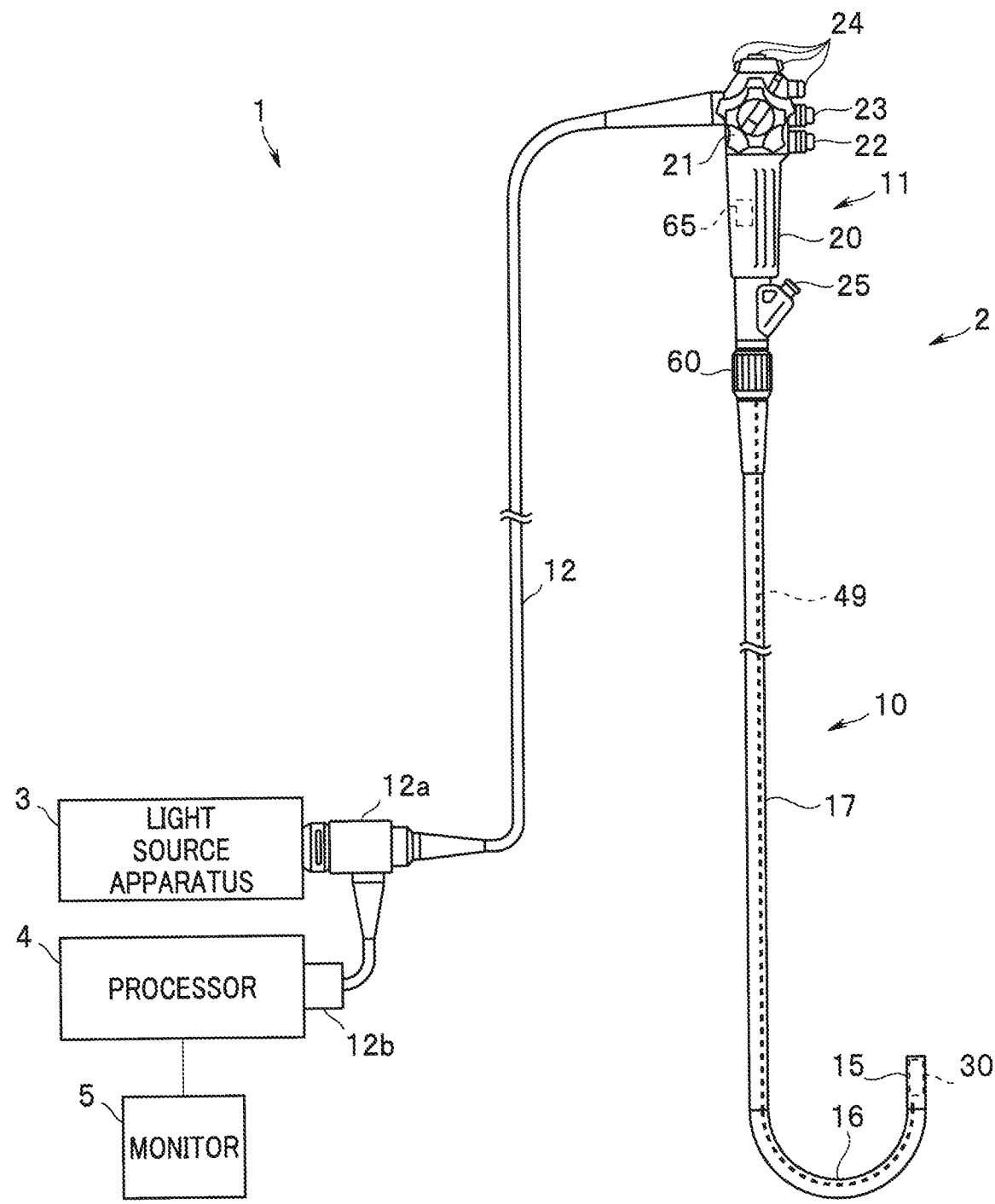
FIG. 1 is a schematic configuration diagram of an endoscope system.

An endoscope system 1 shown in FIG. 1 includes an endoscope 2, a light source apparatus 3 that supplies illumination light to the endoscope 2, a processor 4 that drives and controls an image pickup unit 40 incorporated in the endoscope 2 and processes an image pickup signal transmitted from the image pickup unit 40 and a monitor 5 that receives a video signal outputted from the processor 4 and displays an endoscopic image.

The endoscope 2 includes an elongated insertion portion 10 that can be inserted into a subject/object, an operation portion 11 connected to a proximal end side of the insertion portion 10 and a universal cord 12 that extends from the operation portion 11.

The insertion portion 10 includes a distal end portion 15 disposed at a distal end, a bending portion 16, which is bendable and connected to a proximal end side of the distal end portion 15 and a flexible tube portion 17, which is connected to a proximal end side of the bending portion and flexible.

Here, as shown in FIG. 10, for example, an observation window 15a for observing an inside of a subject/object, illumination windows 15b for irradiating the subject/object with illumination light, a distal end opening portion 15c that has a dual function as a treatment instrument outlet and a suction opening portion and a front water feeding nozzle 15d are disposed on a distal end face of the distal end portion 15. Note that in order to efficiently dispose the respective members at the distal end portion 15, the observation window 15a and the distal end opening portion 15c are disposed side by side in a diameter direction of the distal end face, and thus, an optical axis Oa of the observation window 15a is offset with respect to a central axis (longitudinal axis) 0 of the insertion portion 10.

An operation portion body 20 constituting a grasping portion is provided at the operation portion 11.

A bending operation portion 21 for bending the bending portion 16, an air/water feeding operation portion 22 for feeding air/water through the front water feeding nozzle 15d or the like, a suction operation portion 23 for suctioning through the distal end opening portion 15c, and a plurality of switch portions 24 for mainly operating an image pickup function of the endoscope 2 through a remote operation of the processor 4 or the like are provided on the proximal end side of the operation portion body 20.

A treatment instrument insertion port 25 through which a treatment instrument such as forceps can be inserted into a treatment instrument channel communicating with the distal end opening portion 15c is provided on a distal end side of the operation portion body 20.

The universal cord 12 is constructed of a composite cable in which various cables including a signal cable 40a of the image pickup unit 40 inserted through the insertion portion 10, light guides 41 and a water feeding tube 43 (see FIGS. 8 and 9) are interpolated. A light guide connector 12a and a video connector 12b are provided at an extending end of the universal cord 12, the light guide connector 12a is connected to the light source apparatus 3 and the video connector 12b is connected to the processor 4.

Next, a configuration of the distal end portion 15 will be described in detail with reference to FIG. 2 to FIG. 13.

As shown in FIG. 2, the distal end portion 15 includes a variable distal end portion body 30.

The distal end portion body 30 includes a fixed barrel 31 as a first holding barrel and a movable barrel 32 turnably supported by the fixed barrel 31 as a second holding barrel.

The fixed barrel 31 integrally includes a substantially cylindrical coupling portion 35 couplable with the distal end side of the bending portion 16, a hollow shaft 36 disposed inside the coupling portion 35, and a bridge portion 37 that couples the hollow shaft 36 with an inner circumferential side of the coupling portion 35.

The hollow shaft 36 has both a function for turnably supporting the movable barrel 32 and a function for holding the image pickup unit 40 disposed inside the observation window 15a, and is constructed of a substantially cylindrical member.

For this reason, the hollow shaft 36 is disposed coaxially with the optical axis Oa of the observation window 15a and the image pickup unit 40 is held inside the hollow shaft 36 through bonding or the like.

A distal end side of the hollow shaft 36 protrudes from the distal end of the coupling portion 35 and an outer circumference of the protruding portion of the hollow shaft 36 is, for example, processed into a two-step form. In the protruding portion of the hollow shaft 36, a small-diameter first step region located at a most distal end is set as a fitting portion 36a to fit with the movable barrel 32 and a second step region connected to the proximal end side of the fitting portion 36a is set as a spacer portion 36b for defining a distance from the movable barrel 32 in the optical axis Oa direction.

A stopper ring 38 for maintaining fitting with the movable barrel 32 by the fitting portion 36a is fixed to the outer circumference of the hollow shaft 36 closer to the proximal end side than the spacer portion 36b. The stopper ring 38 integrally includes, for example, a ring body 38a and a ring-shaped flange portion 38b protruding from the ring body 38a, and the flange portion 38b has a pair of cutout grooves 38c (only one cutout groove 38c is illustrated in FIG. 2 to FIG. 4 or the like), for example.

The bridge portion 37 has a pinion shaft hole 37a extending in the optical axis Oa direction at a position close to the hollow shaft 36.

The movable barrel 32 is constructed of a substantially cylindrical member.

The movable barrel 32 has holding holes corresponding to various internal components except the image pickup unit 40. In other words, the movable barrel 32 has light guide holding holes 32b, a channel holding hole 32c and a water feeding tube holding hole 32d at positions corresponding to the illumination windows 15b, the distal end opening portion 15c and the front water feeding nozzle 15d respectively.

The distal end sides of the light guides 41 coupled to an illumination optical system 44 are held to the light guide holding holes 32b. The distal end side of a treatment instrument channel 42 and the distal end side of the water feeding tube 43 are held to the channel holding hole 32c and the water feeding tube holding hole 32d respectively.

The movable barrel 32 has a bearing hole 32a at a position corresponding to the observation window 15a. The fitting portion 36a formed in the hollow shaft 36 of the fixed barrel 31 fits with the bearing hole 32a. In this way, the movable barrel 32 is supported by the fixed barrel 31 so as to be turnable around the optical axis Oa.

A proximal end face of the movable barrel 32 has a pair of hook holding holes 32e and hook members 46 are held to the hook holding holes 32e. The hook members 46 have engaging portions 46a that can engage with the flange portion 38b of the stopper ring 38.

For example, as shown in FIGS. 3 and 4, when the bearing hole 32a of the movable barrel 32 fits with the fitting portion 36a of the fixed barrel 31, each engaging portion 46a is inserted into each cutout groove 38c. When the spacer portion 36b of the fixed barrel 31 comes into contact with the proximal end face of the movable barrel 32 and the movable barrel 32 is turned around the optical axis Oa with respect to the fixed barrel 31 in a predetermined manner, each engaging portion 46a slidably engages with the proximal end face of the flange portion 38b. This prevents the movable barrel 32 from falling off the fixed barrel 31 with movement in the optical axis Oa direction with respect to the fixed barrel 31 prohibited.

An arc-shaped rack gear 47 centered around the optical axis Oa is provided so as to protrude from the proximal end face of the movable barrel 32 so as to extend along the bearing hole 32a.

As shown in FIG. 5, a pinion gear 48 turnably supported by the pinion shaft hole 37a of the fixed barrel 31 meshes with the rack gear 47. A coil pipe wire 49 as a power transmission member inserted through the insertion portion 10 is coupled to the proximal end of the pinion gear 48. The rack gear 47, the pinion gear 48 and the coil pipe wire 49 constitute a power transmission mechanism 50 inside the insertion portion 10, and the power transmission mechanism 50 can transmit power (turning power) transmitted to the coil pipe wire 49 on the operation portion 11 side to the rack gear 47.

Transmission of the turning power through the power transmission mechanism 50 allows the movable barrel 32 that holds the treatment instrument channel 42 or the like to turn around the optical axis Oa without turning the image pickup unit 40.

Here, a pair of stoppers 47a that come into contact with the pinion gear 48 to thereby restrict a turning range of the movable barrel 32 are provided at both ends of the rack gear 47.

For example, as shown in FIG. 6, when the pinion gear 48 is in contact with one stopper 47a, the movable barrel 32 is set so as to be disposed at a reference position where the movable barrel 32 is coaxial with the fixed barrel 31. For example, as shown in FIG. 7, when the pinion gear 48 is in contact with the other stopper 47a, the movable barrel 32 is set so as to be positioned at a maximum turning position with respect to the fixed barrel 31.

In this case, various internal components disposed in the distal end portion 15 are disposed so as to extend substantially linearly along a longitudinal axis O of the insertion portion 10, when the movable barrel 32 is at the reference position as shown, for example, in FIG. 8. On the other hand, various internal components generate deflection with respect to the longitudinal axis O direction, for example, as shown in FIG. 9 to thereby allow the movable barrel 32 to turn with respect to the fixed barrel 31. In this case, in order to reduce interference with various internal components and ensure a sufficient turning angle (maximum turning position) of the movable barrel 32, the coupling portion 35 of the fixed barrel 31 has a partial arc-shaped notch portion 35a at part of the distal end side.

Note that in order to prevent the position of the engaging portion 46a of each hook member 46 from coinciding with the position of each cutout groove 38c within a range in which the movable barrel 32 turns from the reference position defined by the pair of stoppers 47a to the maximum turning position, the stopper ring 38 is fixed to the fixed barrel 31 with the stopper ring 38 being positioned in a rotating direction.

In the distal end portion body 30 configured in this way, the coupling portion 35 of the fixed barrel 31 fits with the inside of a barrel body 55, which also functions as a most distal bending piece, and is thereby non-turnably coupled to the bending portion 16.

The distal end side of the movable barrel 32 is covered with a distal end cover 56. The distal end cover 56 has hole portions 56a to 56d corresponding to the bearing hole 32a, the light guide holding holes 32b, the channel holding hole 32c and the water feeding tube holding hole 32d respectively. Note that in the present embodiment, the observation window 15a is formed of cover glass 57 that water-tightly blocks the bearing hole 32a and the hole portion 56a independently of the image pickup unit 40 as shown, for example, in FIGS. 12 and 13. The illumination window 15b is formed of the illumination optical system 44 exposed from the hole portion 56b as shown, for example, in FIG. 13.

Furthermore, a skin 58 for covering an outer circumference of the distal end portion body 30 is disposed between the barrel body 55 and the distal end cover 56. Both ends of the skin 58 are bonded and fixed to the fixed barrel 31 and the movable barrel 32 via a thread wound bonding portion 58a and the distal end portion body 30 is thereby sealed liquid-tightly.

Here, it is possible to adopt a manual turning operation portion 60 turnably supported by the operation portion body 20 as a power source to transmit power to the coil pipe wire 49 as shown, for example, in FIG. 1. In this case, as shown, for example, in FIG. 14, a rack gear 61 is provided on an inner circumferential side of the turning operation portion 60, a proximal end side of the coil pipe wire 49 is coupled to a pinion gear 62 that meshes with the rack gear 61, and it is thereby possible to transmit turning power inputted to the turning operation portion 60 by an operator or the like to the coil pipe wire 49.

Alternatively, it is also possible to adopt a configuration in which as shown, for example, in FIG. 1, a stepping motor 65 is provided inside the operation portion 11 and the stepping motor 65 is coupled to the proximal end side of the coil pipe wire 49 as a power source for transmitting power to the coil pipe wire 49.

According to such an embodiment, since the endoscope includes the fixed barrel 31 non-turnably provided at the distal end portion 15 of the insertion portion 10, the image pickup unit 40 held to the fixed barrel 31, the channel holding hole 32c that holds the distal end of the treatment instrument channel 42 inserted through the insertion portion 10, the movable barrel 32 supported by the fixed barrel 31 so as to be turnable around the optical axis Oa of the image pickup unit 40 located closer to the distal end side than the fixed barrel 31 and the power transmission mechanism 50 that transmits power to the movable barrel for causing the movable barrel 32 to turn, the endoscope can easily adjust the position of the treatment instrument with respect to a target site under endoscopic observation.

In other words, by holding the image pickup unit 40 to the fixed barrel 31 non-turnably disposed in the distal end portion 15, holding the distal end of the treatment instrument channel 42 or the like to the movable barrel 32 which is turnable around the optical axis Oa of the image pickup unit 40 with respect to the fixed barrel 31 and causing the movable barrel 32 to turn via the power transmission mechanism 50, it is possible to move a treatment instrument 70 protruding from the distal end opening portion 15c around the optical axis Oa via the treatment instrument channel 42 without turning an endoscopic image displayed on the monitor 5 or the like as shown, for example, in FIG. 15.

Therefore, it is possible to move the treatment instrument 70 around the optical axis Oa and access a target site 71 such as an affected area displayed on the endoscopic image without moving or causing to disappear the target site 71.

Note that the present invention is not limited to the embodiment described so far, but various modifications or changes can be made and such modifications or changes also fall within the technical scope of the present invention.

Figure 16:
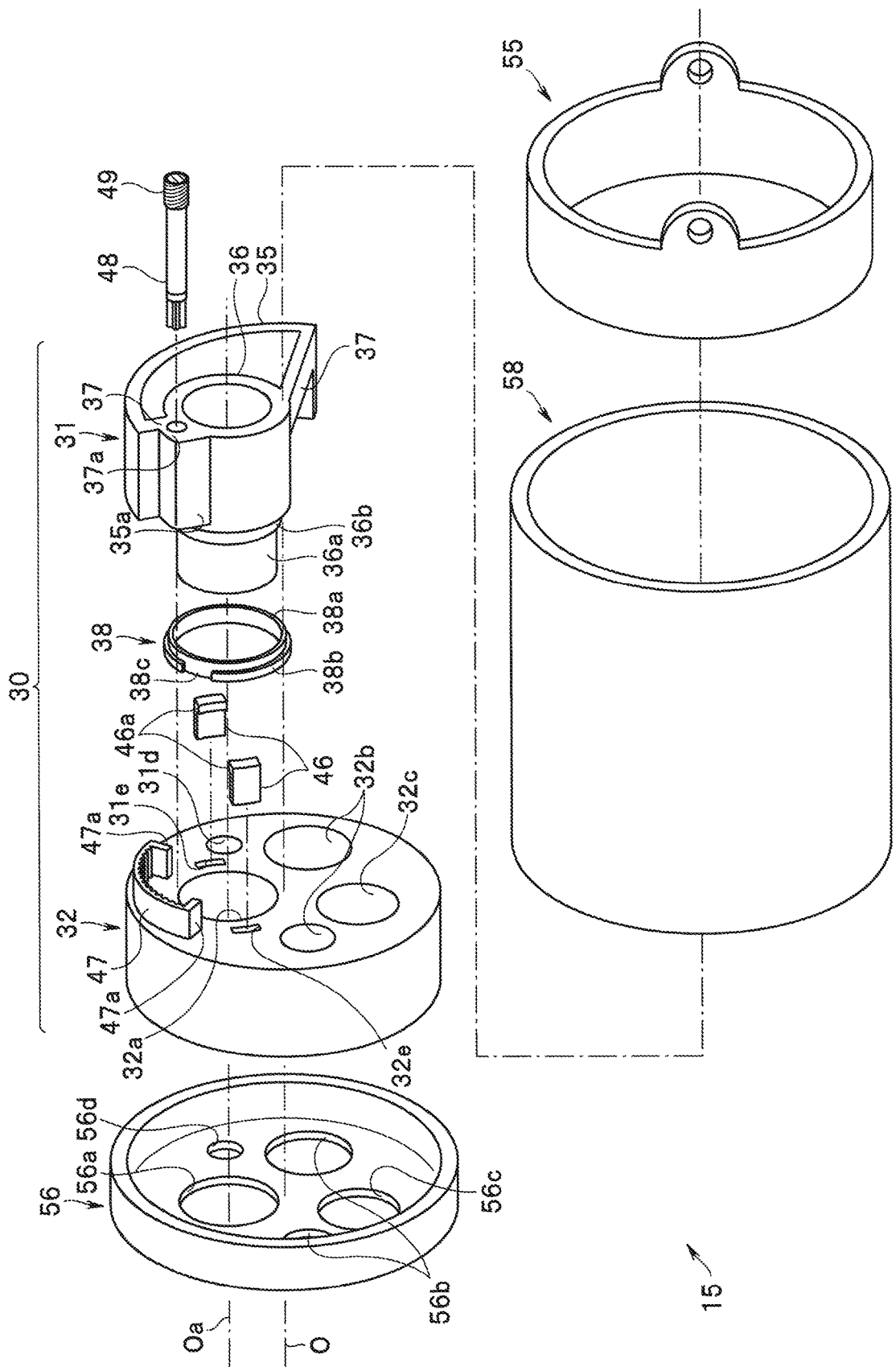
FIG. 16 relates to a first modification and is an exploded perspective view of the distal end portion.

For example, as shown in FIG. 16, the coupling portion 35 provided in the fixed barrel 31 is not limited to a substantially cylindrical member, but a partially cylindrical member can also be adopted. A plurality of bridge portions 37 coupling the coupling portion 35 and the hollow shaft 36 can also be provided. Such a configuration makes it possible to secure coupling strength between the coupling portion 35 and the hollow shaft 36 and more effectively suppress interference between various internal components and the coupling portion 35 when the movable barrel 32 turns.

For example, as shown in FIG. 17 to FIG. 21, the turning range of the movable barrel 32 can also be restricted using rigid internal components disposed in the distal end portion 15 instead of the pair of stoppers 47a provided for the rack gear 47.

Figure 18:
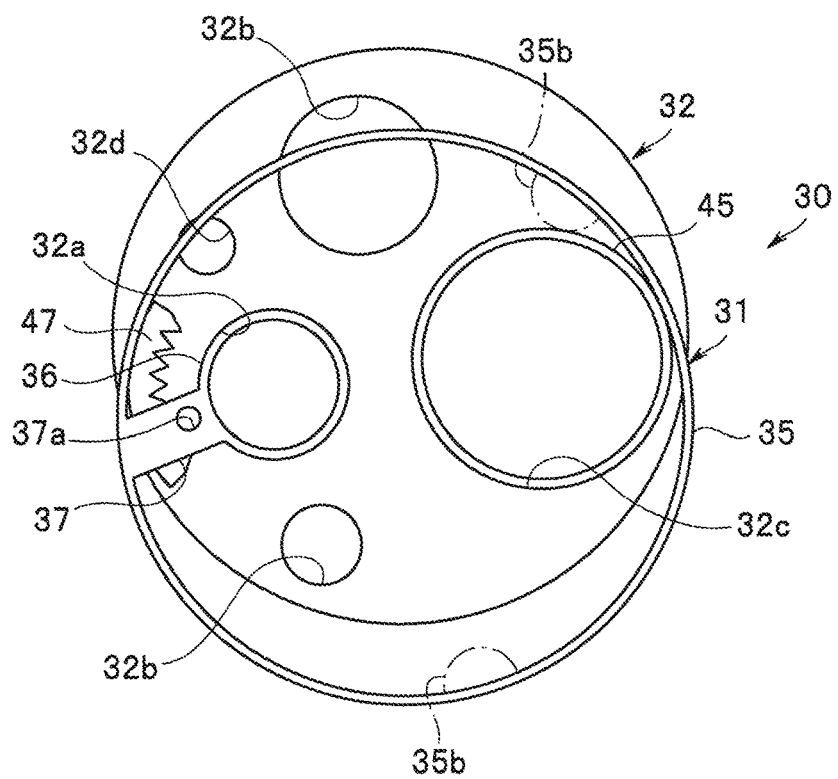
FIG. 18 relates to the second modification and is a rear view illustrating the distal end portion body when the movable barrel is located at the maximum turning position.
Figure 19:
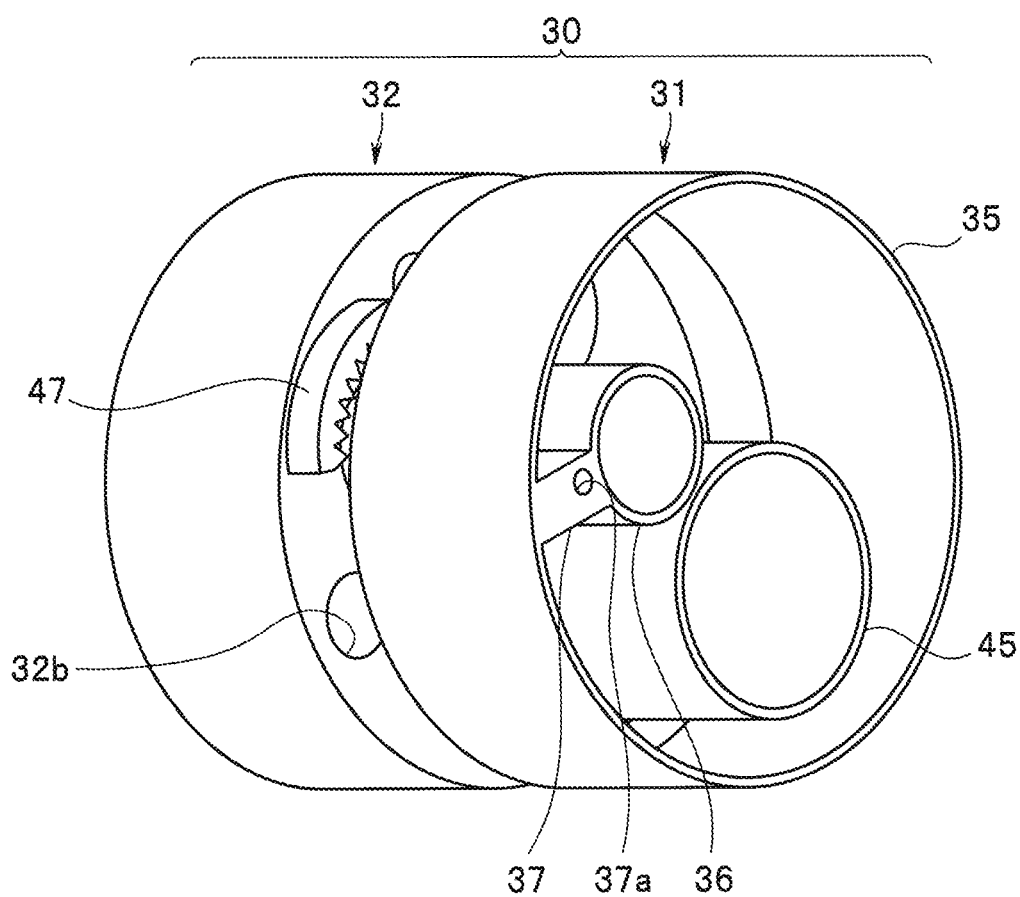
FIG. 19 relates to the second modification and is a perspective view illustrating the distal end portion body when the movable barrel is located at the reference position.
Figure 20:
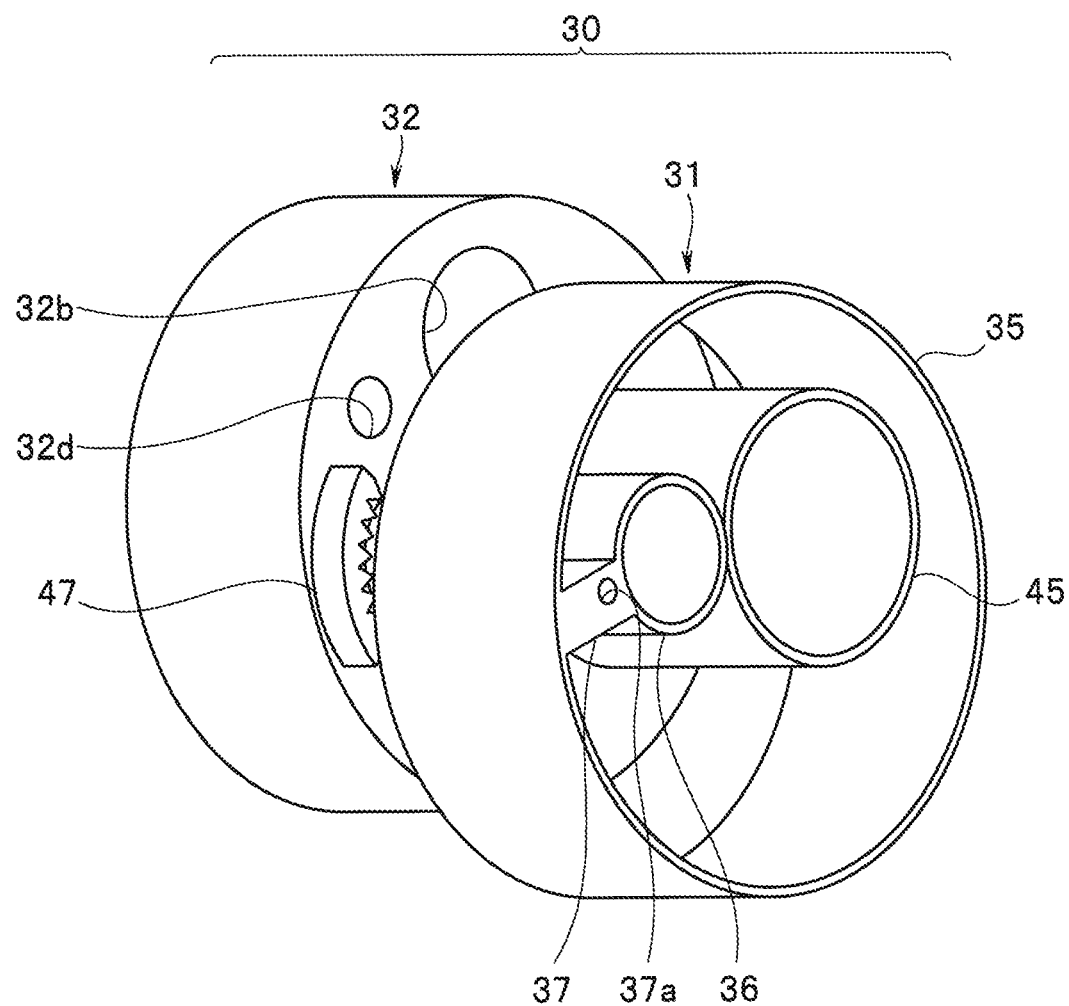
FIG. 20 relates to the second modification and is a perspective view illustrating the distal end portion body when the movable barrel is located at the maximum turning position.
Figure 21:
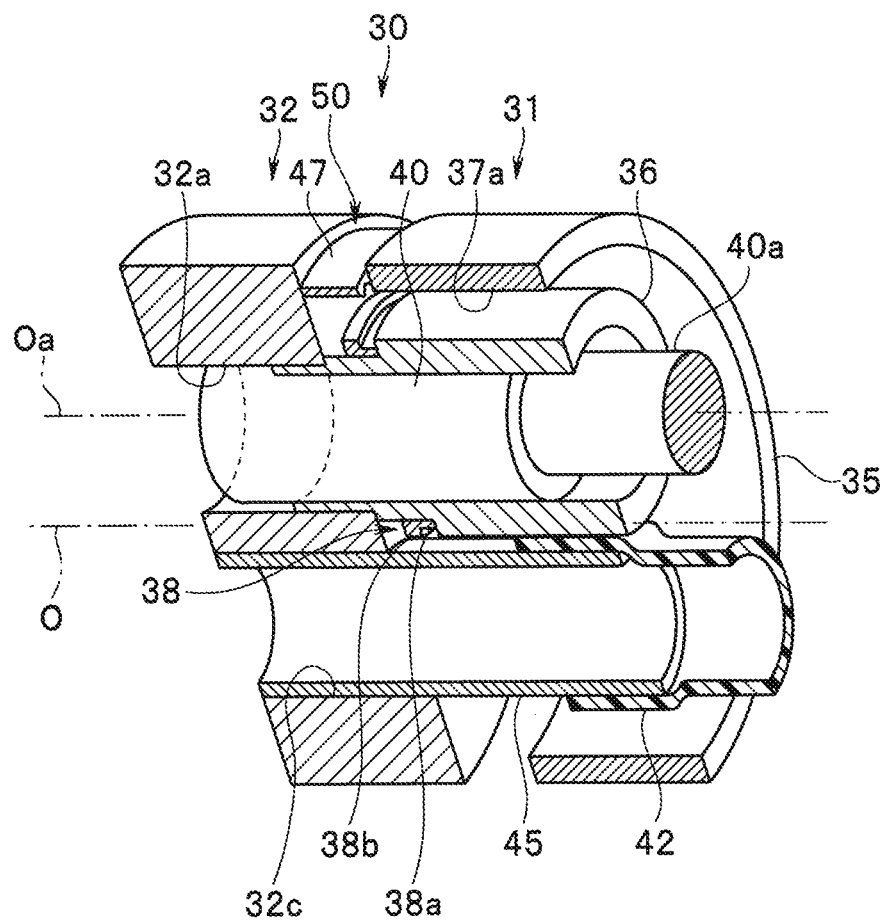
FIG. 21 relates to the second modification and is a cross-sectional view of main parts of the movable distal end portion body along XXI-XXI in FIG. 17.

In other words, as shown, for example, in FIG. 19 to FIG. 21, by extending a rigid channel pipe 45 for holding the distal end side of the treatment instrument channel 42 to the movable barrel 32 to the inside of the coupling portion 35 and causing the channel pipe 45 to come into contact with the inner circumferential surface of the coupling portion 35, it is possible to restrict the turning range of the movable barrel. More specifically, when the movable barrel 32 is located at the reference position (see FIGS. 17, 19 and 21) and the maximum turning position (see FIGS. 18 and 20), by adjusting the position of the channel pipe 45 with respect to the movable barrel 32 so that the channel pipe 45 comes into contact with the inner circumferential surface of the coupling portion 35, it is possible to cause the channel pipe 45 to also function as a stopper.

Figure 17:
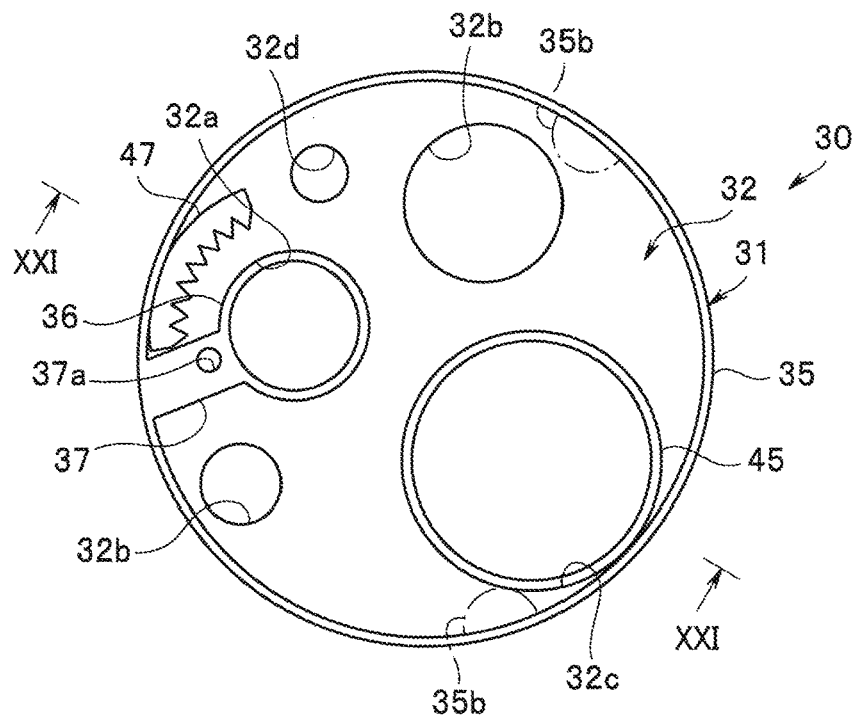
FIG. 17 relates to a second modification and is a rear view illustrating the distal end portion body when the movable barrel is located at the reference position.

In that case, for example, as illustrated by a single-dot dashed line in FIGS. 17 and 18, by providing protrusion portions 35b that can come into contact with the channel pipe 45 on an inner surface of the coupling portion 35 and adjusting a protrusion position and a protrusion amount of the protrusion portion 35b, it is also possible to hold the channel pipe 45 (treatment instrument channel 42) to an appropriate position on the movable barrel 32 and adjust the turning range or the like of the movable barrel 32 with respect to the fixed barrel 31. In this case, the protrusion portion 35b can be formed by providing a thick portion in part of the coupling portion 35 or modifying part of the coupling portion 35 inward.

As the rigid internal component also used as the stopper, the illumination optical system 44 or the like can also be used instead of the channel pipe 45 or together with the channel pipe 45.

What is claimed is:

1. An endoscope comprising:
   a fixed barrel integrally including a coupling portion and a hollow shaft, the coupling portion being non-turnably provided at a distal end portion of an insertion portion, the hollow shaft being disposed inside the coupling portion, the hollow shaft having a protruding portion protruding from a distal end of the coupling portion;
   an image pickup unit held inside the hollow shaft;
   a movable barrel including a holding hole for holding a distal end of a treatment instrument channel inserted through the insertion portion, and a bearing hole with which the protruding portion of the hollow shaft fits, the movable barrel being supported by the fixed barrel so as to be turnable around an optical axis of the image pickup unit by the protruding portion of the hollow shaft fitting within the bearing hole; and
   a power transmission that transmits, to the movable barrel, power for causing the movable barrel to turn.

2. The endoscope according to claim 1, further comprising a power source provided in an operation portion connected to a proximal end of the insertion portion and configured to transmit turning power to the power transmission.

3. The endoscope according to claim 2, wherein the power source is a stepping motor.

4. The endoscope according to claim 2, wherein the power source is a turning operation sleeve turnably supported on the operation portion.

5. The endoscope according to claim 1, further comprising:
- a stopper ring held to the fixed barrel on an outer circumferential side of the image pickup unit; and
- a hook member held to the movable barrel and configured to prohibit movement in a direction of the optical axis of the movable barrel by engagement with the stopper ring.

6. A distal end structure of an endoscope, comprising:
- a fixed barrel integrally including a coupling portion and a hollow shaft, the coupling portion being provided at a distal end of an insertion portion of the endoscope, the hollow shaft being disposed inside the coupling portion, the hollow shaft having a protruding portion protruding from a distal end of the coupling portion;
- an image pickup unit held inside the hollow shaft;
- a movable barrel including a holding hole for holding a distal end of a treatment instrument channel inserted through the insertion portion, and a bearing hole with which the protruding portion of the hollow shafts fits, the movable barrel being supported by the fixed barrel so as to be turnable in a circumferential direction of the image pickup unit with respect to the image pickup unit by the protruding portion of the hollow shaft fitting within the bearing hole; and
- a power transmission that transmits, to the movable barrel, power for causing the movable barrel to turn.

7. The distal end structure of the endoscope according to claim 6, wherein the movable barrel is supported by the fixed barrel so as to be turnable around an optical axis of the image pickup unit.

8. The distal end structure of the endoscope according to claim 7, further comprising a power source provided in an operation portion connected to a proximal end of the insertion portion and configured to transmit turning power to the power transmission.

9. The distal end structure of the endoscope according to claim 8, wherein the power source is a stepping motor.

10. The distal end structure of the endoscope according to claim 8, wherein the power source is a turning operation sleeve turnably supported on the operation portion.

11. The distal end structure of the endoscope according to claim 10, further comprising:
- a stopper ring held to the fixed barrel on an outer circumferential side of the image pickup unit; and
- a hook member held to the movable barrel and configured to prohibit movement in a direction of the optical axis of the movable barrel by engagement with the stopper ring.

12. A method for modifying a distal end structure of an endoscope comprising:
- a fixed barrel integrally including a coupling portion and a hollow shaft, the coupling portion being provided at a distal end of an insertion portion of the endoscope, the hollow shaft being disposed inside the coupling portion, the hollow shaft having a protruding portion protruding from a distal end of the coupling portion;
- an image pickup unit held inside the hollow shaft;
- a movable barrel including a holding hole for holding a distal end of a treatment instrument channel inserted through the insertion portion, and a bearing hole with which the protruding portion of the hollow shaft fits, the movable barrel being supported by the fixed barrel so as to be turnable in a circumferential direction of the image pickup unit with respect to the image pickup unit by the protruding portion of the hollow shaft fitting within the bearing hole; and
- a power transmission that transmits, to the movable barrel, power for causing the movable barrel to turn, the method comprising:
- causing the movable barrel to turn via the power transmission without causing the image pickup unit held to the fixed barrel to turn; and
- moving a treatment instrument protruding from the treatment instrument channel by turning the movable barrel and causing the treatment instrument to access a target site.

* * * * *